United States Patent [19]

White

[11] Patent Number: 4,784,641

[45] Date of Patent: Nov. 15, 1988

[54] ARTICLE AND METHOD FOR THE ORAL DOSING OF FLUIDIC MATERIAL TO PATIENTS

[75] Inventor: Douglas J. White, Oceanport, N.J.

[73] Assignee: Bio-Pak Associates, Farmingdale, N.J.

[21] Appl. No.: 62,128

[22] Filed: Jun. 12, 1987

[51] Int. Cl.⁴ .............................................. A61M 3/00

[52] U.S. Cl. ........................................ 604/77; 128/360; 215/11.1

[58] Field of Search ................. 604/77, 218, 236, 239, 604/264; 128/359, 360; 215/11 R, 11 E

[56] References Cited

U.S. PATENT DOCUMENTS

| | | | |
|---|---|---|---|
| 26,327 | 11/1859 | La Forme | 215/11 R |
| 97,659 | 12/1869 | Lockwood | 215/11 R |
| 587,939 | 8/1897 | Decker | 215/11.1 |
| 950,710 | 3/1910 | Williams | 215/11 R |
| 1,175,054 | 3/1916 | Dunfee | 215/11.1 |
| 1,518,823 | 12/1924 | Schmidt | 215/11 R |
| 1,634,170 | 6/1927 | Brown | 215/11.1 |
| 1,797,433 | 3/1931 | McCrea | 215/11.1 |
| 2,303,997 | 12/1942 | Hogg | 215/11 R |
| 2,469,489 | 5/1949 | Allen et al. | 215/11 R |
| 2,600,978 | 6/1952 | Demarco, Jr. | 215/11.1 |
| 3,426,755 | 2/1969 | Clegg | 604/77 |
| 3,572,337 | 3/1971 | Schunk | 604/77 |
| 4,127,126 | 11/1978 | Schunk | 604/77 |
| 4,176,754 | 12/1979 | Miller | 215/11 E |
| 4,545,491 | 10/1985 | Bisgaard et al. | 215/11 R |

FOREIGN PATENT DOCUMENTS

| | | | |
|---|---|---|---|
| 3826 | 8/1891 | Switzerland | 215/11.1 |

*Primary Examiner*—Stephen C. Pellegrino
*Assistant Examiner*—Ralph Lewis
*Attorney, Agent, or Firm*—Lerner, David, Littenberg, Krumholz & Mentlik

[57] ABSTRACT

A syringe and method for the oral administration of fluidic material to a patient are disclosed. The syringe includes a cannula at the dispensing end thereof, which cannula is of sufficient size and shape to approximate a nipple so as to provide a feeding surface which encourages normal sucking by a patient. The cannula is provided with a restricted metering aperture at its downstream end to limit the flow rate of fluidic material from the syringe in order to prevent gagging of the patient and to allow the patient to safely draw fluidic material from the syringe in a controlled manner.

20 Claims, 2 Drawing Sheets

ARTICLE AND METHOD FOR THE ORAL DOSING OF FLUIDIC MATERIAL TO PATIENTS

FIELD OF THE INVENTION

The present invention relates to oral dosing devices and methods and, more particularly, to a syringe and to a method employing the syringe for the oral administration of fluidic material to a patient.

BACKGROUND OF THE INVENTION

It has been found advantageous to utilize a syringe for the oral administration of fluidic material, for example liquid medicine or food, to infant, aged or incapacitated persons and to small animals and pets, which often require the same degree of care as infants. As used herein, the term "patients" thus is intended to cover infants, aged or incapacitated persons, small animals (whether wild or being cared for by veterinarians or zoos) and domestic pets (e.g. fish, birds, reptiles and other species). Typically, such an oral dispensing device includes an elongate barrel within which is slidably disposed a reciprocating piston. The piston is reciprocated within the barrel by means of an elongate plunger, and the dispensing end of the barrel includes a tip portion through which the medication is injected into the mouth. Examples of such syringes are shown in the prior issued U.S. Pat. Nos. 3,572,337 and 4,127,126, of George J. Schunk. In addition, conventional syringes in which the hypodermic needles or catheters have been removed have been commonly used to orally administer liquid medicine to such patients.

Heretofore, when it has been desired to administer liquid medicine to such patients, the tip of the syringe has been inserted into the patient's mouth and the medicine was injected by depressing the plunger, whereby the medicine is forceably passed from the barrel through the tip at a rate that is essentially controlled by the force exerted by the user on the plunger.

The foregoing prior art standard oral dosing syringes required forceful opening of the patient's mouth in order to allow the medication to be introduced, causing rejection by the patient and spilling of the medication, and often required the patient to be restrained during the administration of the medication. In addition, the high rate of speed of injection employed often caused the patient, particularly infant children, to gag or choke during the administration of the medication.

It is, therefore, a primary object of the present invention to provide an improved oral dosing syringe for use with patients, who may be infants, aged or incapacitated persons, animals or other pets, which syringe allows medication or fluidic foods to be dispensed safely, carefully and in a controlled manner.

Another object of the present invention is to provide an oral dosing syringe having a cannula at the dispensing end thereof which is of such size and shape as to provide a feeding surface for patients to suck on and draw medicine, food, or the like, from the syringe.

A further object of the invention is to provide an improved oral dosing syringe having a nipple-like cannula at the dispensing end thereof which is provided with a metered dispensing aperture therein to prevent the flow of medication or food from the syringe at a rate high enough to cause gagging of the patient.

Further objects and advantages of the invention will become apparent as the following description proceeds.

SUMMARY OF THE INVENTION

Briefly stated and in accordance with one embodiment of this invention, an improved oral dosing device comprises a syringe having a cannula at the dispensing end thereof, which cannula is of sufficient size and shape to approximate a nipple so as to provide a feeding surface for an infant to suck on. The cannula may be provided with a restricted metering aperture at its downstream end to limit the flow rate of medication or food from the syringe in order to prevent gagging of the patient and to allow the patient to draw the medicine or food from the syringe. The applicant's cannula or nipple tip is comfortable, simulates breast feeding and is readily acceptable by infants and small children, as well as by aged and incapacitated persons, small animals and pets. The nipple tip encourages normal sucking, and allows medication or food to be dispensed safely, carefully and in a controlled manner.

Briefly stated and in accordance with another embodiment of this invention, an improved method of oral dosing infant, aged or incapacitated persons and small animals and pets comprises providing a syringe having a barrel and a plunger, said syringe further including a cannula constructed and arranged to simulate a nipple positioned at the dispensing end thereof and having a metering aperture at its downstream end, the syringe being filled with a desired dosage of fluidic material; inserting the cannula into the patient's mouth so that the patient may suck on the cannula; and gently depressing the plunger into the barrel to dispense the fluidic material from the metering aperture while the patient sucks on the cannula.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION OF THE INVENTION

Figure 1:
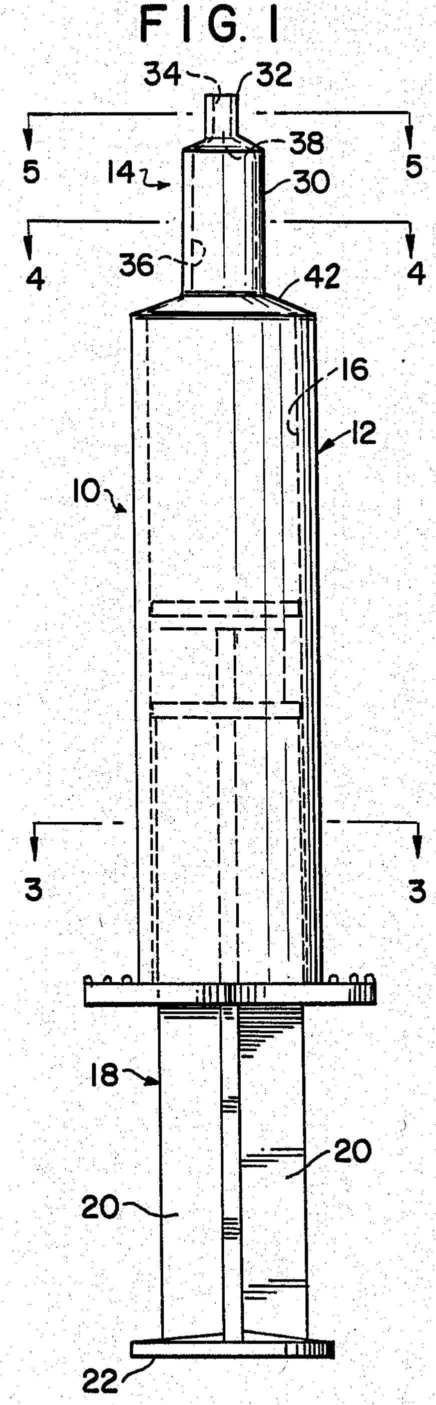
FIG. 1 is a side elevation view illustrating an oral dosing syringe having a nipple-like cannula at the dispensing end thereof.
Figure 2:
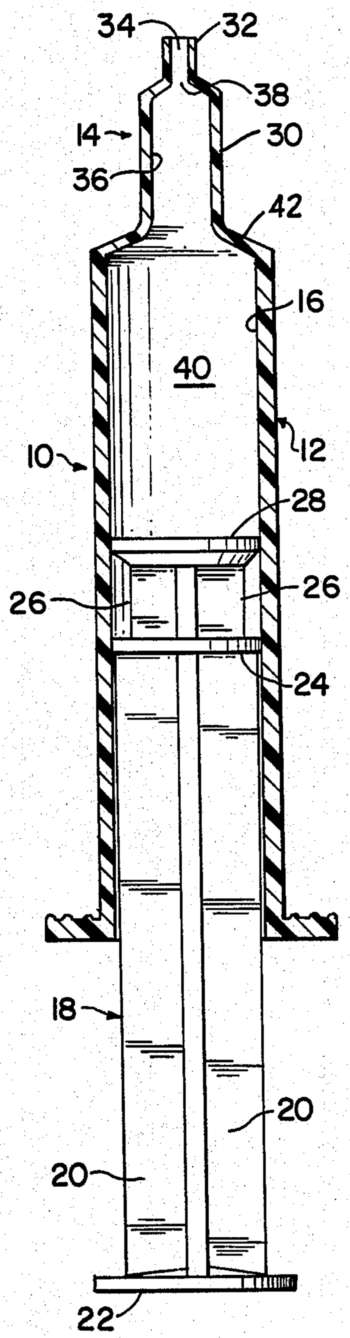
FIG. 2 is a vertical cross-sectional view taken through the oral dosing syringe of FIG. 1.
Figure 5:
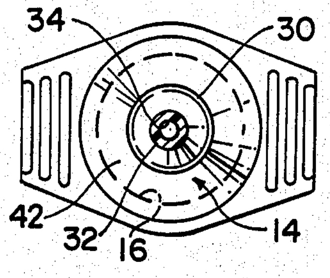
FIGS. 3, 4 and 5 are cross-sectional views taken substantially on respective lines 3—3, 4—4 and 5—5 shown in FIG. 1 of the drawings.
Figure 4:
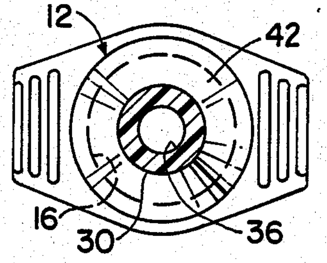
Figure 3:
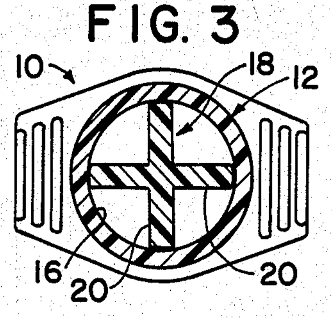

Turning now to FIGS. 1-5 of the drawings, wherein similar reference characters designate corresponding parts throughout the several views, there is illustrated an oral dosing syringe, shown generally at 10, which is preferably formed of rigid synthetic plastic material.

The syringe preferably comprises a cylindrical main body portion 12 and a cannula or nozzle portion 14 disposed at the dispensing end of the main body portion. The main body portion 12 and cannula 14 preferably have a unitary, integral construction for safety reasons (to prevent the cannula from being injected into the patients mouth and causing choking or gagging of the patient), and so as to prevent leakage of fluids therefrom and to provide a smooth and uninterrupted surface to a patient. Syringe body portion 12 includes an elongate barrel 16 within which is slidably disposed a plunger or piston rod member 18, formed of rigid synthetic plastic material. The plunger 18 is comprised of right-angled ribs or flanges 20 which extend substantially the length thereof and are axially connected together. At their lower ends, the ribs 20 have a hand or thumb engaging disc 22 secured thereto, at right angles to the length of the plunger.

Spaced from its upper end, the plunger 18 has a disc 24 integral with the ribs 20, and the plunger above the disc 24 is provided with ribs or flanges 26 similar to the ribs 20 but having a shorter cross sectional length than the ribs 20. At their upper ends, the ribs 26 support a piston or head member 28 of inverted disc-shaped formation which is sufficiently pliable at its periphery to slidably and sealingly engage the inner wall of the syringe barrel 16.

The cannula or nozzle portion 14 of syringe 10 includes an elongate, relatively wide, base or sucking portion 30 and a short, relatively narrow tip or metering portion 32 which is provided with an axially oriented metering aperture 34 of pre-determined cross-sectional area. The base portion 30 and tip portion 32 of the cannula are hollow and provided with respective passageways 36 and 38 which intercommunicate the metering aperture 34 with a chamber 40 formed by the barrel 16 and piston member 28 of the syringe, such that medication entrapped in chamber 40 (between the piston 28 and the walls of barrel 16) will be dispensed from aperture 34 at a controlled rate when the plunger 18 is pushed into barrel 16 during usage of the syringe.

The cannula or nozzle 14 is constructed and arranged to be of such size and shape that it approximates a nipple, in order to provide a feeding surface for patients to suck on, allowing them to draw medication from the syringe while the operator gently pushes plunger 18 into barrel 16. To this end, it has been found desirable to provide the base or sucking portion 30 of the cannula with a cross sectional diameter in the range of from about 3/16 of an inch to about 7/16 of an inch, preferably ⅜ of an inch, and to provide the tip or metering portion 32 of the cannula with a cross-sectional diameter in the range of from about 3/32 of an inch to about 3/16 of an inch, preferably ⅛ of an inch. Similarly, it has been found that the best results are obtained when the length of the base portion 30 is in the range of from about ½ of an inch to about ¾ of an inch, preferably 11/16 of an inch, and when the length of the tip portion 32 is in the range of from about ⅛ of an inch to about ¼ of an inch, preferably 3/16 of an inch. The metering aperture 34 has a diameter in the range of from about 1/32 of an inch to about 3/32 of an inch and, preferably, is about 1/16 of an inch, to insure that, under normal pressure on plunger 18, the medication flow rate through aperture 34 will not cause the patient to gag.

In general, it has been found that best results can be obtained with oral dosing syringe 10 when the ratio of the length of the base portion 30 to the length of the tip portion 32 is equal to or greater than 3, and when the ratio of the diameter of the base portion 30 to the diameter of the tip portion 32 is equal to or exceeds 2. The foregoing dimensions and relationships provide for a nipplelike cannula which is comfortable, simulates breast feeding and is readily acceptable by infants and small children, as well as by aged and incapacitated persons and small animals and pets. The nipple-like cannula and its metering aperture encourage normal sucking, which allows medication and food to be dispensed safely, carefully and in a controlled manner.

It should be noted that the main body portion 12 of the syringe 10 has an outside diameter that is in the range of from about ⅝ of an inch to one inch, preferably 13/16 of an inch, and a length in the range of about 3 inches to about 3.5 inches, preferably 3 and 1/16 inches. The outside diameter of the main body portion 12 is also preferably at least twice as large as the outside diameter of the cannula 14. The difference in ranges of outside diameters of the cannula 14 and the main body portion 12 allows a shoulder 42 to be formed at the junction of the two members. The shoulder 42 provides a convenient abutment which prevents the patient from drawing the body portion 12 of the syringe into his mouth and causing consequent gagging or choking. Also, it serves as a convenient guide to the person dispensing the medication, letting that person know when the cannula 14 has been inserted to a proper depth into the patient's mouth.

Figure 6:
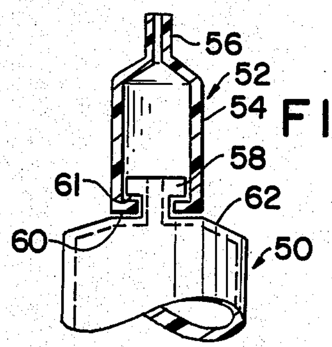
FIG. 6 is a side elevation view, with portions cut away for clarity, of a portion of an oral closing syringe, showing an alternate embodiment of this invention.

Referring now to FIG. 6, an embodiment of the present invention has been shown in which a lip 60 on the cannula, shown generally at 52, is forcibly snapped into engagement with a groove or detent 61 on the cylindrical main body portion, shown generally at 50, of the syringe. The lip 60 amd groove 61 detent arrangement is constructed and arranged to require greater pressure than is normally generated within the syringe to force the cannula off of the main body portion of the syringe but yet allow the cannula to be removed manually by prying in order to facilitate removal of the cannula from the main body portion in connection with cleaning and changing the size of the cannula to accommodate different patients.

The cannula 52 includes a base or sucking portion 54 and a tip or metering portion 56 similar to that described in connection with the embodiment of FIGS. 1–5. However, in the embodiment of FIG. 6, instead of the cannula being integral with the main body portion of the syringe, it is forcibly snapped on to a grooved extension 58, carried by the downstream end of the syringe body 50, by means of the lip 60 formed on the upstream internal surface of the cannula 52 and the groove 61 on extension 58. The cannula 52 in this embodiment is snapped on tightly so that it is in near abutment with or abuts against a shoulder 62 on syringe body 50, locking itself thereto until sufficient prying or unlocking force is applied to unsnap it.

Figure 7:
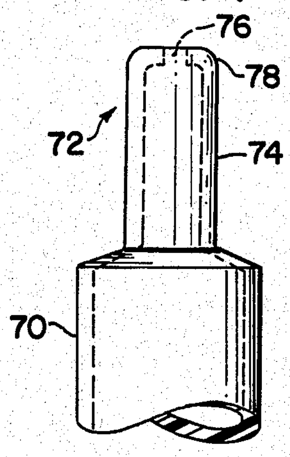
FIG. 7 is a side elevation view of a portion of an oral dosing syringe, showing another embodiment of this invention.

Referring now to FIG. 7, another embodiment of the oral dosing syringe has there been illustrated which includes a syringe body portion, shown generally at 70, and an integral cannula portion, shown generally at 72. The cannula 72, although provided with a base or sucking portion 74, is also provided with a metering aperture 76 in an end wall 78 thereof which end wall replaces the tip portions 32 and 56 of the embodiments shown in FIGS. 1 and 6, respectively. The metering aperture 76 in this embodiment serves a similar function to that performed by the aperture 34 in tip portion 32 of the FIG. 1 embodiment and is suitably dimensioned to restrict the flow of medication from the syringe to a rate that avoids patient gagging and facilitates the patient's drawing of medication or food from the syringe while the user of the syringe gently depresses the plunger thereof.

Figure 8:
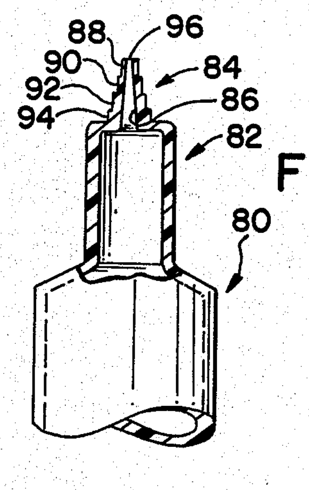
FIG. 8 is a side elevation view, with portions cut away for clarity, of a portion of an oral dosing device, showing yet another embodiment of this invention.

Referring now to FIG. 8, yet another embodiment of the oral dosing syringe has there been illustrated, which syringe includes a syringe body portion, shown generally at 80, and an integral cannula portion, shown generally at 82. In this case the cannula 82 includes a somewhat longer tip or metering portion 84 than that shown and described in connection with the embodiment of FIGS. 1–5. The elongated metering portion 84 includes a tapered interior passageway 86 and an outer surface that includes a plurality of stepped portions 88, 90, 92 and 94 therein, at each of which the outer diameter of the metering portion increases relative to the stepped portion immediately downstream thereof. The arrangement is such that the metering portion 84 can be selectively severed at one or another of the stepped portions 88, 90, 92 and 94 to provide an aperture at the new end thereof that is larger than the aperture 96 that is formed at the uncut end of the metering portion 84. This allows the user to conveniently use the syringe in connection with providing more viscous medication and food to patients than would normally be the case, or to provide higher flow rates of medication and food to patients that can accept such greater flow rates.

The method of using the syringe to administer liquid medicine or other fluidic material into the mouth of an infant, aged or incapacitated person or other patient will now be considered with reference to the use of a syringe of the type shown in FIGS. 1–5. Initially, the plunger 18 is depressed, to place the piston 28 adjacent the downstream end of barrel 16. The cannula 14 is then inserted into a vial of liquid medicine, and plunger 18 is retracted from barrel 16 to draw the liquid medicine into the chamber 40 of the barrel.

After a predetermined amount of liquid medicine has been drawn into barrel 40, the cannula 14 is withdrawn from the vial and gently inserted into the patient's mouth, between the patient's gums or teeth, to facilitate the patient's sucking on the base portion 30 of the cannula. The plunger 20 is then depressed, to begin injecting the medicine into the patient's mouth concurrently with the patient's sucking on the cannula. This step is continued until all of the medication has been transferred from chamber 40 to the patient's mouth, at which time the cannula is removed from the patient's mouth.

From the foregoing description, it can be seen that the present invention provides several important advantages. It provides an improved oral dosing syringe for use with infant, aged or incapacitated persons and other patients which allows medication to be dispensed safely, carefully and in a controlled manner. The cannula is of such a size and shape as to provide a feeding surface for patients to suck on and draw medicine from the syringe without having the spillage and trauma that accompanies the conventional force feeding of medication to such patients. Moreover, the metered aperture at the dispensing end of the cannula insures that the flow rate of medication from the syringe will be insufficient to cause gagging of the patient.

While there have been shown and described what are presently considered to be the preferred embodiments of this invention, it will be obvious to those skilled in the art that various changes and modifications may be made without departing from the broader aspects of this invention. For example, in the embodiment of FIG. 6, wherein the cannula 52 is detachable from the syringe body 50, it might be desirable when used with some patients to have the cannula made of a material that is more flexible than the rigid synthetic plastic material contemplated for the syringe body 50 and such a change would be considered to be within the intent of this invention. Also, although the outer surfaces of the outer body 12 and the sucking portion 30 and metering portion 32 of the cannula 14 have been described as being generally cylindrical, these surfaces may be slightly tapered, or conical, to facilitate manufacture of the syringe for example, without departing from this invention. It is, therefore, aimed in the appended claims to cover all such changes and modifications that fall within the true spirit and scope of this invention.

What is claimed is:

1. A syringe for the oral administration of fluidic material to a patient, comprising:

(a) an elongate hollow barrel for holding a dosage of fluidic material, said barrel having a predetermined outside diameter and having an upstream end and a downstream end;

(b) a reciprocative plunger operatively connected to a piston slidably received within said barrel from the upstream end thereof; and (c) a hollow, generally cylindrical cannula formed as a continuation of and integral with said barrel at the downstream end thereof and in axial alignment therewith, said cannula having an upstream sucking portion and having an outside diameter at its upstream end that is no greater than about one-half of said predetermined outside diameter of said barrel at the downstream end thereof to thereby form a shoulder between said downstream end of said barrel and said upstream end of said cannula which serves to assist in limiting penetration of said cannula into the patient's mouth during usage, said cannula being provided with a metering aperture means at its downstream end having an inner diameter less than the inner diameter of said upstream sucking portion to restrict the flow of fluidic material therefrom, under normal hand pressure on said plunger, to a level that is insufficient to cause gagging of said patient during oral administration of fluidic material to said patient, said cannula further having a predetermined length so as to provide a sucking surface for the patient during usage.

2. A syringe according to claim 1, in which said predetermined outside diameter of said barrel is in the range of from about ⅝ of an inch to about 1 inch; and in which the length of said cannula is in the range of from about ⅝ of an inch to about 1 inch.

3. A syringe according to claim 2, in which said metering aperture has a diameter in the range of from about 1/32 of an inch to about 3/32 of an inch.

4. A syringe according to claim 2, in which the sucking portion of said cannula has an outside diameter in the range of from about 3/16 of an inch to about 7/16 of an inch.

5. A syringe according to any one of claims 2, 3 or 4, in which the outside diameter of said barrel is about 13/16 of an inch.

6. A syringe for the oral administration of fluidic material to a patient, comprising:

(a) an elongate hollow barrel for holding a dosage of fluidic material, said barrel having an upstream end and a downstream end;

(b) a reciprocative plunger operatively connected to a piston slidably received within said barrel from the upstream end thereof; and (c) a hollow cannula carried by said barrel at the downstream end thereof and in axial alignment therewith, said cannula including a generally cylindrical, elongate upstream sucking portion having a first predetermined outside diameter sized to fit within a patient's mouth and a downstream generally cylindrical, shorter metering portion having a metering aperture therein, said metering portion having a second predetermined outside diameter, said second predetermined outside diameter being no greater than about $\frac{1}{2}$ of said first predetermined diameter, and the length of said metering portion being no greater than about $\frac{1}{3}$ of the length of said sucking portion, whereby said cannula presents a nipple-like appearance conductive to inducing a sucking action by a patient to whom fluidic material is being orally administered and the flow rate of fluidic material from said cannula to the patient, under normal hand pressure on said plunger, is restricted to a level that is insufficient to cause gagging of the patient.

7. A syringe according to claim 6, in which said metering aperture has a diameter in the range of about 1/32 of an inch to about 3/32 of an inch.

8. A syringe according to claim 6, in which said first predetermined outside diameter is in the range of from 3/16 of an inch to about 7/16 of an inch.

9. A syringe according to claim 6, in which the length of said cannula is in the range of from about 5/8 of an inch to about 1 inch.

10. A syringe according to any one of claims 6, 7, 8 or 9, in which the length of said sucking portion is in the range of from about $\frac{1}{2}$ of an inch to about $\frac{3}{4}$ of an inch and the length of said metering portion is in the range of about $\frac{1}{8}$ of an inch to $\frac{1}{4}$ of an inch.

11. A syringe according to claim 10 in which the length of said sucking portion is about 11/16 of an inch and the length of said metering portion is about 3/16 of an inch.

12. A syringe according to any one of claims 6, 7, 8 or 9, in which said cannula is detachably connected to said barrel.

13. A syringe for the oral administration of fluidic material to a patient, comprising:

(a) an elongate hollow barrel for holding a dosage of fluidic material, said barrel having an upstream end and a downstream end;

(b) a reciprocative plunger operatively connected to a piston slidably received within said barrel from the upstream end thereof; and (c) a hollow, cannula carried by said barrel at the downstream end thereof and in axial alignment therewith, said cannula inclusing a generally cylindrical elongate upstream sucking portion having a predetermined diameter and having a metering aperture adjacent the downstream end thereof, whereby said cannula presents an appearance conductive to inducing a sucking action by a patient two whom fluidic material is being orally administered, said metering aperture having a predetermined diameter less than the internal diameter of said upstream sucking portion so as to restrict the flow of fluidic material therefrom, under normal hand pressure on said plunger, to a level that is insufficient to cause gagging of said patient during oral administration of fluidic material to said patient, and said barrel and said cannula having a unitary construction so as to prevent leakage of said fluidic material therefrom and to provide a smooth and uninterrupted surface to said patient.

14. A syringe according to claim 13, in which said predetermined diameter of said cannula sucking portion is in the range of from about 3/16 of an inch to about 7/16 of an inch; and in which said predetermined diameter of said metering aperture is in the range of from about 1/32 of an inch to about 3/32 of an inch.

15. A syringe according to claim 14 in which the length of said cannula is in the range of from about 5/8 of an inch to about 1 inch.

16. A syringe according to any one of claims 2, 9 or 15, in which the length of said cannula is about 7/8 of an inch.

17. A syringe according to any one of claims 3, 7 or 14, in which said metering aperture has a diameter of about 1/16 of an inch.

18. A syringe according to any one of claims 4, 8 or 14, in which said sucking portion has an outside diameter of about 3/8 of an inch.

19. A syringe according to any one of claims 1 or 13, wherein said cannula includes a downstream metering portion having a generally tapered passageway therein that decreases in diameter from an upstream portion thereof to a downstream portion thereof and that communicates with said metering aperture, said metering portion having an outer surface thereon that decreases in diameter from an upstream part thereof to a downstream part thereof, whereby said metering portion may be selectively served along said surface to selectively increase the diameter of said metering aperture.

20. A syringe according to claim 19, wherein said outer surface of said metering portion includes a plurality of stepped cylindrical portions thereon having different diameters from one another, said diameters decreasing from said upstream part to said downstream part of said metering portion.

* * * * *

UNITED STATES PATENT AND TRADEMARK OFFICE

CERTIFICATE OF CORRECTION

PATENT NO. : 4,784,641

DATED : November 15, 1988

INVENTOR(S) : Douglas J. White

It is certified that error appears in the above-identified patent and that said Letters Patent is hereby corrected as shown below:

Column 7, line 18, "conductive" should read --conducive--.
Column 8, line 1, "inclusing" should read --including--.
Column 8, lines 5,6, "con-ductive" should read --con-ducive--.
Column 8, line 47, "served" should read --severed--.

Signed and Sealed this

Sixteenth Day of May, 1989

*Attest:*

DONALD J. QUIGG

*Attesting Officer* *Commissioner of Patents and Trademarks*